United States Patent [19]
Krueger et al.

[11] Patent Number: 5,492,931
[45] Date of Patent: Feb. 20, 1996

[54] CYCLOALKYLCARBOXANILIDES

[75] Inventors: Bernd-Wieland Krueger; Klaus Sasse; Thomas Schenke, all of Bergisch Gladbach; Michael Negele, Solingen; Heinz-Wilhelm Dehne, Monheim, all of Germany

[73] Assignee: Bayer Aktiengesellschaft, Leverkusen, Germany

[21] Appl. No.: 185,430

[22] Filed: Jan. 21, 1994

[30] Foreign Application Priority Data

Jan. 28, 1993 [DE] Germany ............ 43 02 305.3

[51] Int. Cl.⁶ ............ A01N 37/18; C07C 233/58
[52] U.S. Cl. ............ 514/613; 514/623; 514/624; 514/628; 564/191; 564/190; 564/189
[58] Field of Search ............ 564/191; 514/613, 514/623, 624, 628

[56] References Cited

U.S. PATENT DOCUMENTS

| | | | |
|---|---|---|---|
| 3,277,171 | 10/1966 | Hopkins | 564/191 |
| 4,166,735 | 9/1979 | Pilgram et al. | 71/118 |
| 4,675,342 | 6/1987 | McGovern et al. | 514/613 |
| 4,710,518 | 12/1987 | Kurahashi et al. | 514/624 |
| 5,059,623 | 10/1991 | Krüger et al. | 564/191 |

FOREIGN PATENT DOCUMENTS 2377999  8/1978  Germany.

*Primary Examiner*—Shailendra Kumar
*Attorney, Agent, or Firm*—Sprung Horn Kramer & Woods

[57] ABSTRACT

This invention relates to cycloalkylcarboxanilides of the formula

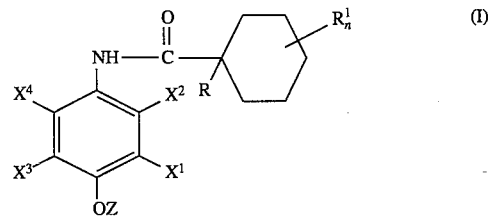

in which
R represents halogen or halogenoalkyl,
$R^1$ represents halogen, alkyl or halogenoalkyl,
n represents the numbers 0, 1, 2 or 3,
$X^1$, $X^2$, $X^3$ and $X^4$ independently of one another represent hydrogen, halogen, alkyl, halogenoalkyl, alkoxy, halogenoalkoxy, alkylthio or halogenoalkylthio, and
Z represents hydrogen,
which have the utility as pesticides and fungicides.

7 Claims, No Drawings

CYCLOALKYLCARBOXANILIDES

The present invention relates to new cycloalkylcarboxanilides, to a process for their preparation, and to their use for combating pests.

It has already been disclosed that a large number of cycloalkylcarboxanilides have fungicidal properties (cf. EP-OS (European Published Specification) 0,416,365 and EP-OS (European Published Specification) 0,416,359). 4-Acetyloxy-2,3-dichloro-(1-methyl-cyclohexanecarboxylic acid) anilide, for example, can be used for combating fungi. The activity of this substance is good, however, when used at low application rates, it leaves something to be desired in some cases.

New cycloalkylcarboxanilides of the formula

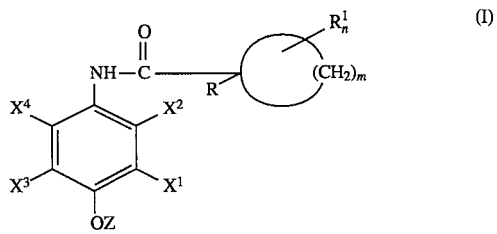

in which
R represents halogen or halogenoalkyl,
$R^1$ represents halogen, alkyl or halogenoalkyl,
m represents integers from 2 to 7,
n represents the numbers 0, 1, 2 or 3,
$X^1$, $X^2$, $X^3$ and $X^4$ independently of one another represent hydrogen, halogen, alkyl, halogenoalkyl, alkoxy, halogenoalkoxy, alkylthio or halogenoalkylthio, and
Z represents hydrogen or the radicals of the formulae

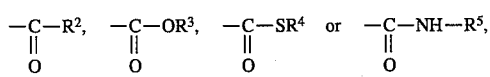

in which
$R^2$ represents alkyl, halogenoalkyl, alkenyl, halogenoalkenyl, alkoxyalkyl, polyalkoxyalkyl, alkylthioalkyl, alkylcarbonyloxyalkyl, alkenylcarbonyloxyalkyl, optionally substituted cycloalkyl, optionally substituted phenyl, optionally substituted phenylalkyl or optionally substituted phenoxyalkyl,
$R^3$ represents alkyl, halogenoalkyl, alkenyl, halogenoalkenyl, alkoxyalkyl, polyalkoxyalkyl, alkylthioalkyl, alkylcarbonyloxyalkyl, alkenylcarbonyloxyalkyl, optionally substituted cycloalkyl, optionally substituted phenyl, optionally substituted phenylalkyl or optionally substituted phenoxyalkyl,
$R^4$ represents alkyl, halogenoalkyl, alkenyl, halogenoalkenyl, alkoxyalkyl, polyalkoxyalkyl, alkylthioalkyl, alkylcarbonyloxyalkyl, alkenylcarbonyloxyalkyl, optionally substituted cycloalkyl, optionally substituted phenyl, optionally substituted phenylalkyl or optionally substituted phenoxyalkyl, and
$R^5$ represents alkyl, halogenoalkyl, alkenyl, halogenoalkenyl, alkoxyalkyl, polyalkoxyalkyl, alkylthioalkyl, alkylcarbonyloxyalkyl, alkenylcarbonyloxyalkyl, optionally substituted cycloalkyl, optionally substituted phenyl, optionally substituted phenylalkyl or optionally substituted phenoxyalkyl,
have now been found.

Furthermore, it has been found that cycloalkylcarboxanilides of the formula (I) are obtained when aminophenols of the formula

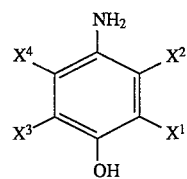

in which
$X^1$, $X^2$, $X^3$ and $X^4$ have the abovementioned meanings, are reacted with cycloalkylcarboxylic acid derivatives of the formula

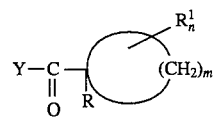

in which
R, $R^1$, m and n have the abovementioned meanings and
Y represents a leaving group,
if appropriate in the presence of an acid-binding agent and if appropriate in the presence of a diluent and, if appropriate, the resulting cycloalkylcarboxanilides of the formula

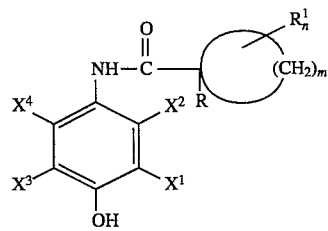

in which
R, $R^1$, m, n, $X^1$, $X^2$, $X^3$ and $X^4$ have the abovementioned meanings,
are reacted either
a) with carboxylic acid halides of the formula

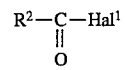

in which
$R^2$ has the abovementioned meaning and $Hal^1$ represents halogen,
if appropriate in the presence of an acid-binding agent and if appropriate in the presence of a diluent,
or
b) with halogenoformic esters of the formula

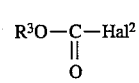

in which
$R^3$ has the abovementioned meaning and $Hal^2$ represents halogen,
if appropriate in the presence of an acid-binding agent and if appropriate in the presence of a diluent,
or
c) with halogenoformic thioesters of the formula

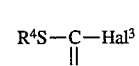

in which
$R^4$ has the abovementioned meaning and $Hal^3$ represents halogen,
if appropriate in the presence of an acid-binding agent and if appropriate in the presence of a diluent, or d) with isocyanates of the formula
R⁵-NCO (VII)

in which

R⁵ has the abovementioned meaning,
if appropriate in the presence of a diluent and if appropriate in the presence of a catalyst.

Finally, it has now been found that the cycloalkylcarboxanilides of the formula (I) according to the invention are highly suitable for combating pests, in particular fungi.

Surprisingly, the cycloalkylcarboxanilides according to the invention have a better fungicidal activity than 4-acetyloxy-2,3-dichloro-(1-methyl-cyclohexanecarboxylic acid) anilide, which is a previously known active substance of similar constitution and the same direction of action.

The cycloalkylcarboxanilides according to the invention are generally known by the formula (I).

R preferably represents fluorine, chlorine, bromine, iodine or halogenoalkyl having 1 to 3 carbon atoms and 1 to 5 identical or different halogen atoms.

R¹ preferably represents fluorine, chlorine, bromine, straight-chain or branched alkyl having 1 to 4 carbon atoms or halogenoalkyl having 1 to 3 carbon atoms and 1 to 5 identical or different halogen atoms.

m preferably represents integers from 2 to 6.

n preferably also represents the numbers 0, 1, 2 and 3. If n represents 2 or 3, the radicals R¹ can be identical or different.

X¹ preferably represents hydrogen, fluorine, chlorine, bromine, iodine, straight-chain or branched alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms or halogenoalkylthio having 1 to 3 carbon atoms and 1 to 5 identical or different halogen atoms.

X² preferably represents hydrogen, fluorine, chlorine, bromine, iodine, straight-chain or branched alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms or halogenoalkylthio having 1 to 3 carbon atoms and 1 to 5 identical or different halogen atoms.

X³ preferably represents hydrogen, fluorine, chlorine, bromine, iodine, straight-chain or branched alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms or halogenoalkylthio having 1 to 3 carbon atoms and 1 to 5 identical or different halogen atoms.

X⁴ preferably represents hydrogen, straight-chain or branched alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms or halogenoalkylthio having 1 to 3 carbon atoms and 1 to 5 identical or different halogen atoms.

Z preferably also represents hydrogen or the radicals of the formulae

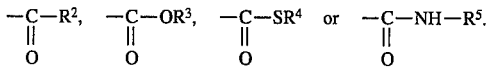

R² preferably represents straight-chain or branched alkyl having 1 to 6 carbon atoms, halogenoalkyl having 1 to 6 carbon atoms and 1 to 7 identical or different halogen atoms, alkenyl having 2 to 6 carbon atoms, halogenoalkenyl having 2 to 6 carbon atoms and 1 to 7 identical or different halogen atoms, alkoxyalkyl having 1 to 6 carbon atoms in the alkyl moiety and 1 to 6 carbon atoms in the alkoxy moiety, alkoxyalkoxyalkyl having 1 to 6 carbon atoms in the alkyl moiety and 1 to 6 carbon atoms in each alkoxy moiety, alkylthioalkyl having 1 to 6 carbon atoms in the alkyl moiety and 1 to 6 carbon atoms in the alkylthio moiety, alkylcarbonyloxyalkyl having 1 to 6 carbon atoms in the alkyl moiety and 1 to 6 carbon atoms in the oxyalkyl moiety, alkenylcarbonyloxyalkyl having 2 to 6 carbon atoms in the alkenyl moiety and 1 to 6 carbon atoms in the oxyalkyl moiety, or represents cycloalkyl having 3 to 8 carbon atoms which is optionally monosubstituted to trisubstituted by identical or different substituents from the series consisting of halogen and/or alkyl having 1 to 4 carbon atoms, or represents phenyl which can be monosubstituted to trisubstituted by identical or different substituents from the series consisting of halogen, alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms and/or halogenoalkylthio having 1 to 3 carbon atoms and 1 to 5 identical or different halogen atoms, or represents phenylalkyl having 1 to 4 carbon atoms in the alkyl moiety, it being possible for the phenyl moiety to be monosubstituted to trisubstituted by identical or different substituents from the series consisting of halogen, alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms and/or halogenoalkylthio having 1 to 3 carbon atoms and 1 to 5 identical or different halogen atoms, or represents phenoxyalkyl having 1 to 4 carbon atoms in the alkyl moiety, it being possible for the phenyl moiety to be monosubstituted to trisubstituted by identical or different substituents from the series consisting of halogen, alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 3 identical or different halogen atoms, alkylthio having 1 to 4 carbon atoms and/or halogenoalkylthio having 1 to 3 carbon atoms and 1 to 5 identical or different halogen atoms.

R³ preferably represents straight-chain or branched alkyl having 1 to 6 carbon atoms, halogenoalkyl having 1 to 6 carbon atoms and 1 to 7 identical or different halogen atoms, alkenyl having 2 to 6 carbon atoms, halogenoalkenyl having 2 to 6 carbon atoms and 1 to 7 identical or different halogen atoms, alkoxyalkyl having 1 to 6 carbon atoms in the alkyl moiety and 1 to 6 carbon atoms in the alkoxy moiety, alkoxyalkoxyalkyl having 1 to 6 carbon atoms in the alkyl moiety and 1 to 6 carbon atoms in each alkoxy moiety, alkylthioalkyl having 1 to 6 carbon atoms in the alkyl moiety and 1 to 6 carbon atoms in the alkylthio moiety, alkylcarbonyloxyalkyl having 1 to 6 carbon atoms in the alkyl moiety and 1 to 6 carbon atoms in the oxyalkyl moiety, alkenylcarbonyloxyalkyl having 2 to 6 carbon atoms in the alkenyl moiety and 1 to 6 carbon atoms in the oxyalkyl moiety, or represents cycloalkyl having 3 to 8 carbon atoms which is optionally monosubstituted to trisubstituted by identical or different substituents from the series consisting of halogen and/or alkyl having 1 to 4 carbon atoms, or represents phenyl which can be monosubstituted to trisubstituted by identical or different substituents from the series consisting of halogen, alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms and/or halogenoalkylthio having 1 to 3 carbon atoms and 1 to 5 identical or different halogen atoms, or represents phenylalkyl having 1 to 4 carbon atoms in the alkyl moiety, it being possible for the phenyl moiety to be monosubstituted to trisubstituted by identical or different substituents from the series consisting of halogen, alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms and/or halogenoalkylthio having 1 to 3 carbon atoms and 1 to 5 identical or different halogen atoms, or represents phenoxyalkyl having 1 to 4 carbon atoms in the alkyl moiety, it being possible for the phenyl moiety to be monosubstituted to trisubstituted by identical or different substituents from the series consisting of halogen, alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 3 identical or different halogen atoms, alkylthio having 1 to 4 carbon atoms and/or halogenoalkylthio having 1 to 3 carbon atoms and 1 to 5 identical or different halogen atoms.

$R^4$ preferably represents straight-chain or branched alkyl having 1 to 6 carbon atoms, halogenoalkyl having 1 to 6 carbon atoms and 1 to 7 identical or different halogen atoms, alkenyl having 2 to 6 carbon atoms, halogenoalkenyl having 2 to 6 carbon atoms and 1 to 7 identical or different halogen atoms, alkoxyalkyl having 1 to 6 carbon atoms in the alkyl moiety and 1 to 6 carbon atoms in the alkoxy moiety, alkoxyalkoxyalkyl having 1 to 6 carbon atoms in the alkyl moiety and 1 to 6 carbon atoms in each alkoxy moiety, alkylthioalkyl having 1 to 6 carbon atoms in the alkyl moiety and 1 to 6 carbon atoms in the alkylthio moiety, alkylcarbonyloxyalkyl having 1 to 6 carbon atoms in the alkyl moiety and 1 to 6 carbon atoms in the oxyalkyl moiety, alkenylcarbonyloxyalkyl having 2 to 6 carbon atoms in the alkenyl moiety and 1 to 6 carbon atoms in the oxyalkyl moiety, or represents cycloalkyl having 3 to 8 carbon atoms which is optionally monosubstituted to trisubstituted by identical or different substituents from the series consisting of halogen and/or alkyl having 1 to 4 carbon atoms, or represents phenyl which can be monosubstituted to trisubstituted by identical or different substituents from the series consisting of halogen, alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms and/or halogenoalkylthio having 1 to 3 carbon atoms and 1 to 5 identical or different halogen atoms, or represents phenylalkyl having 1 to 4 carbon atoms in the alkyl moiety, it being possible for the phenyl moiety to be monosubstituted to trisubstituted by identical or different substituents from the series consisting of halogen, alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms and/or halogenoalkylthio having 1 to 3 carbon atoms and 1 to 5 identical or different halogen atoms, or represents phenoxyalkyl having 1 to 4 carbon atoms in the alkyl moiety, it being possible for the phenyl moiety to be monosubstituted to trisubstituted by identical or different substituents from the series consisting of halogen, alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 3 identical or different halogen atoms, alkylthio having 1 to 4 carbon atoms and/or halogenoalkylthio having 1 to 3 carbon atoms and 1 to 5 identical or different halogen atoms.

$R^5$ preferably represents straight-chain or branched alkyl having 1 to 6 carbon atoms, halogenoalkyl having 1 to 6 carbon atoms and 1 to 7 identical or different halogen atoms, alkenyl having 2 to 6 carbon atoms, halogenoalkenyl having 2 to 6 carbon atoms and 1 to 7 identical or different halogen atoms, alkoxyalkyl having 1 to 6 carbon atoms in the alkyl moiety and 1 to 6 carbon atoms in the alkoxy moiety, alkoxyalkoxyalkyl having 1 to 6 carbon atoms in the alkyl moiety and 1 to 6 carbon atoms in each alkoxy moiety, alkylthioalkyl having 1 to 6 carbon atoms in the alkyl moiety and 1 to 6 carbon atoms in the alkylthio moiety, alkylcarbonyloxyalkyl having 1 to 6 carbon atoms in the alkyl moiety and 1 to 6 carbon atoms in the oxyalkyl moiety, alkenylcarbonyloxyalkyl having 2 to 6 carbon atoms in the alkenyl moiety and 1 to 6 carbon atoms in the oxyalkyl moiety, or represents cycloalkyl having 3 to 8 carbon atoms which is optionally monosubstituted to trisubstituted by identical or different substituents from the series consisting of halogen and/or alkyl having 1 to 4 carbon atoms, or represents phenyl which can be monosubstituted to trisubstituted by identical or different substituents from the series consisting of halogen, alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms and/or halogenoalkylthio having 1 to 3 carbon atoms and 1 to 5 identical or different halogen atoms, or represents phenylalkyl having 1 to 4 carbon atoms in the alkyl moiety, it being possible for the phenyl moiety to be monosubstituted to trisubstituted by identical or different substituents from the series consisting of halogen, alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms and/or halogenoalkylthio having 1 to 3 carbon atoms and 1 to 5 identical or different halogen atoms, or represents phenoxyalkyl having 1 to 4 carbon atoms in the alkyl moiety, it being possible for the phenyl moiety to be monosubstituted to trisubstituted by identical or different substituents from the series consisting of halogen, alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 3 identical or different halogen atoms, alkylthio having 1 to 4 carbon atoms and/or halogenoalkylthio having 1 to 3 carbon atoms and 1 to 5 identical or different halogen atoms.

R particularly preferably represents fluorine, chlorine, bromine, iodine, trifluoromethyl, trichloromethyl, difluoromethyl, fluoromethyl and fluorochloromethyl.

R¹ particularly preferably represents fluorine, chlorine, bromine, methyl, ethyl, n-propyl, isopropyl, n-butyl, tert.-butyl, trifluoromethyl, trichloromethyl, difluoromethyl, fluoromethyl and fluorochloromethyl.

m particularly preferably represents integers from 2 to 6, in particular 4 or 5.

n particularly preferably also represents the numbers 0, 1, 2 or 3.

$X^1$ particularly preferably represents hydrogen, fluorine, chlorine, bromine, iodine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and trifluoromethylthio.

$X^2$ particularly preferably represents hydrogen, fluorine, chlorine, bromine, iodine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and trifluoromethylthio.

$X^3$ particularly preferably represents hydrogen, fluorine, chlorine, bromine, iodine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and trifluoromethylthio.

$X^4$ particularly preferably represents hydrogen, fluorine, chlorine, bromine, iodine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and trifluoromethylthio.

Z particularly preferably also represents hydrogen or the radicals of the formulae

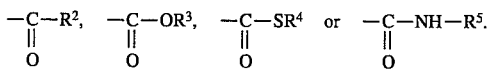

$R^2$ particularly preferably represents straight-chain or branched alkyl having 1 to 4 carbon atoms, halogenoalkyl having 1 or 2 carbon atoms and 1 to 3 fluorine, chlorine and/or bromine atoms, alkenyl having 2 to 4 carbon atoms, halogenoalkenyl having 2 to 4 carbon atoms and 1 to 3 fluorine, chlorine and/or bromine atoms, alkoxyalkyl having 1 to 4 carbon atoms in the alkyl moiety and 1 to 4 carbon atoms in the alkoxy moiety, alkoxyalkoxyalkyl having 1 to 4 carbon atoms in the alkyl moiety and 1 to 4 carbon atoms in each alkoxy moiety, alkylthioalkyl having 1 to 4 carbon atoms in the alkyl moiety and 1 to 4 carbon atoms in the alkylthio moiety, alkylcarbonyloxyalkyl carbonyloxyalkyl having 1 to 4 carbon atoms in the alkyl moiety and 1 to 4 carbon atoms in the oxyalkyl moiety, alkenylcarbonyloxyalkyl having 2 to 4 carbon atoms in the alkenyl moiety and 1 to 4 carbon atoms in the oxyalkyl moiety, or represents cycloalkyl having 3 to 7 carbon atoms which is optionally monosubstituted to trisubstituted by identical or different substituents from the series consisting of fluorine, chlorine, bromine, methyl, ethyl, n-propyl, isopropyl, n-butyl and/or tert.-butyl, or represents phenyl which can be monosubstituted to trisubstituted by identical or different substituents from the series consisting of fluorine, chlorine, bromine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and/or trifluoromethylthio, or represents phenylalkyl having 1 or 2 carbon atoms in the alkyl moiety, it being possible for the phenyl moiety to be monosubstituted to trisubstituted by identical or different substituents from the series consisting of fluorine, chlorine, bromine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and/or trifluoromethylthio, or represents phenoxyalkyl having 1 or 2 carbon atoms in the alkyl moiety, it being possible for the phenyl moiety to be monosubstituted to trisubstituted by identical or different substituents from the series consisting of fluorine, chlorine, bromine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and/or trifluoromethylthio.

$R^3$ particularly preferably represents straight-chain or branched alkyl having 1 to 4 carbon atoms, halogenoalkyl having 1 or 2 carbon atoms and 1 to 3 fluorine, chlorine and/or bromine atoms, alkenyl having 2 to 4 carbon atoms, halogenoalkenyl having 2 to 4 carbon atoms and 1 to 3 fluorine, chlorine and/or bromine atoms, alkoxyalkyl having 1 to 4 carbon atoms in the alkyl moiety and 1 to 4 carbon atoms in the alkoxy moiety, alkoxyalkoxyalkyl having 1 to 4 carbon atoms in the alkyl moiety and 1 to 4 carbon atoms in each alkoxy moiety, alkylthioalkyl having 1 to 4 carbon atoms in the alkyl moiety and 1 to 4 carbon atoms in the alkylthio moiety, alkylcarbonyloxyalkyl having 1 to 4 carbon atoms in the alkyl moiety and 1 to 4 carbon atoms in the oxyalkyl moiety, alkenylcarbonyloxyalkyl having 2 to 4 carbon atoms in the alkenyl moiety and 1 to 4 carbon atoms in the oxyalkyl moiety, or represents cycloalkyl having 3 to 7 carbon atoms which is optionally monosubstituted to trisubstituted by identical or different substituents from the series consisting of fluorine, chlorine, bromine, methyl, ethyl, n-propyl, isopropyl, n-butyl and/or tert.-butyl, or represents phenyl which can be monosubstituted to trisubstituted by identical or different substituents from the series consisting of fluorine, chlorine, bromine, methyl, ethyl, n-propyl, tert.-butyl, trifluoromethyl, trichloromethyl, difluoromethyl, fluoromethyl, fluorochloromethyl, methoxy, ethoxy, trifluoromethoxy, methylthio, ethylthio and/or trifluoromethylthio, or represents phenylalkyl having 1 or 2 carbon atoms in the alkyl moiety, it being possible for the phenyl moiety to be monosubstituted to trisubstituted by identical or different substituents from the series consisting of fluorine, chlorine, bromine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and/or trifluoromethylthio, or represents phenoxyalkyl having 1 or 2 carbon atoms in the alkyl moiety, it being possible for the phenyl moiety to be monosubstituted to trisubstituted by identical or different substituents from the series consisting of fluorine, chlorine, bromine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and/or trifluoromethylthio.

$R^4$ particularly preferably represents straight-chain or branched alkyl having 1 to 4 carbon atoms, halogenoalkyl having 1 or 2 carbon atoms and 1 to 3 fluorine, chlorine and/or bromine atoms, alkenyl having 2 to 4 carbon atoms, halogenoalkenyl having 2 to 4 carbon atoms and 1 to 3 fluorine, chlorine and/or bromine atoms, alkoxyalkyl having 1 to 4 carbon atoms in the alkyl moiety and 1 to 4 carbon atoms in the alkoxy moiety, alkoxyalkoxyalkyl having 1 to 4 carbon atoms in the alkyl moiety and 1 to 4 carbon atoms in each alkoxy moiety, alkylthioalkyl having 1 to 4 carbon atoms in the alkyl moiety and 1 to 4 carbon atoms in the alkylthio moiety, alkylcarbonyloxyalkyl having 1 to 4 carbon atoms in the alkyl moiety and 1 to 4 carbon atoms in the oxyalkyl moiety, alkenylcarbonyloxyalkyl having 2 to 4 carbon atoms in the alkenyl moiety and 1 to 4 carbon atoms in the oxyalkyl moiety, or represents cycloalkyl having 3 to 7 carbon atoms which is optionally monosubstituted to trisubstituted by identical or different substituents from the series consisting of fluorine, chlorine, bromine, methyl, ethyl, n-propyl, isopropyl, n-butyl and/or tert.-butyl, or represents phenyl which can be monosubstituted to trisubstituted by identical or different substituents from the series consisting of fluorine, chlorine, bromine, methyl, ethyl, n-propyl, tert.-butyl, trifluoromethyl, trichloromethyl, difluoromethyl, fluoromethyl, fluorochloromethyl, methoxy, ethoxy, trifluoromethoxy, methylthio, ethylthio and/or trifluoromethylthio, or represents phenylalkyl having 1 or 2 carbon atoms in the alkyl moiety, it being possible for the phenyl moiety to be monosubstituted to trisubstituted by identical or different substituents from the series consisting of fluorine, chlorine, bromine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and/or trifluoromethylthio, or represents phenoxyalkyl having 1 or 2 carbon atoms in the alkyl moiety, it being possible for the phenyl moiety to be monosubstituted to trisubstituted by identical or different substituents from the series consisting of fluorine, chlorine, bromine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and/or trifluoromethylthio.

$R^5$ particularly preferably represents straight-chain or branched alkyl having 1 to 4 carbon atoms, halogenoalkyl having 1 or 2 carbon atoms and 1 to 3 fluorine, chlorine and/or bromine atoms, alkenyl having 2 to 4 carbon atoms, halogenoalkenyl having 2 to 4 carbon atoms and 1 to 3 fluorine, chlorine and/or bromine atoms, alkoxyalkyl having 1 to 4 carbon atoms in the alkyl moiety and 1 to 4 carbon atoms in the alkoxy moiety, alkoxyalkoxyalkyl having 1 to 4 carbon atoms in the alkyl moiety and 1 to 4 carbon atoms in each alkoxy moiety, alkylthioalkyl having 1 to 4 carbon atoms in the alkyl moiety and 1 to 4 carbon atoms in the alkylthio moiety, alkylcarbonyloxyalkyl having 1 to 4 carbon atoms in the alkyl moiety and 1 to 4 carbon atoms in the oxyalkyl moiety, alkenylcarbonyloxyalkyl having 2 to 4 carbon atoms in the alkenyl moiety and 1 to 4 carbon atoms in the oxyalkyl moiety, or represents cycloalkyl having 3 to 7 carbon atoms which is optionally monosubstituted to trisubstituted by identical or different substituents from the series consisting of fluorine, chlorine, bromine, methyl, ethyl, n-propyl, isopropyl, n-butyl and/or tert.-butyl, or represents phenyl which can be monosubstituted to trisubstituted by identical or different substituents from the series consisting of fluorine, chlorine, bromine, methyl, ethyl, n-propyl, tert.-butyl, trifluoromethyl, trichloromethyl, difluoromethyl, fluoromethyl, fluorochloromethyl, methoxy, ethoxy, trifluoromethoxy, methylthio, ethylthio and/or trifluoromethylthio, or represents phenylalkyl having 1 or 2 carbon atoms in the alkyl moiety, it being possible for the phenyl moiety to be monosubstituted to trisubstituted by identical or different substituents from the series consisting of fluorine, chlorine, bromine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and/or trifluoromethylthio, or represents phenoxyalkyl having 1 or 2 carbon atoms in the alkyl moiety, it being possible for the phenyl moiety to be monosubstituted to trisubstituted by identical or different substituents from the series consisting of fluorine, chlorine, bromine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio and/or trifluoromethylthio.

Very particularly preferred compounds are compounds of the formula (I) with the above mentioned definitions in which m represents integers from 5 to 6, n represents 0, $X_1$ represents chlorine, $X_2$ represents chlorine, R represents chlorine, bromine and trifluoromethyl.

If 4-amino-2,3-dichlorophenol and 1-bromo-cyclohexanecarboxylic acid chloride are used as starting substances, the course of the process according to the invention (first step) can be illustrated by the following equation:

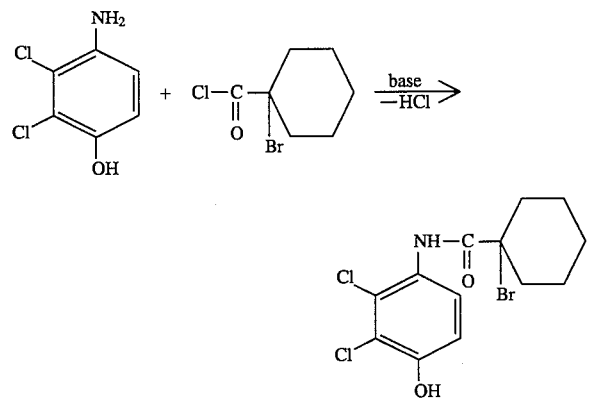

If 4-(1-bromo-cyclohexanoyl)-amino-2,3-dichloro-phenol is used as starting substance and acetyl chloride as reactant, the course of the process according to the invention (second step, variant a) can be illustrated by the following equation:

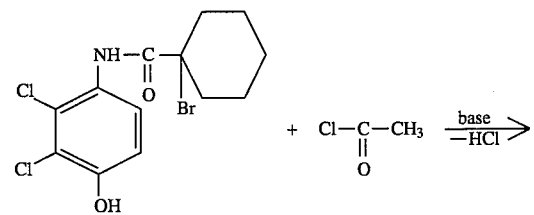

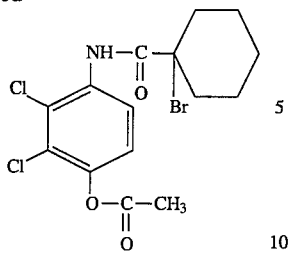

If 4-(1-bromo-cyclohexanoyl)-amino-2,3-dichloro-phenol is used as starting substance and methyl chloroformate as reactant, the course of the process according to the invention (second step, variant b) can be illustrated by the following equation:

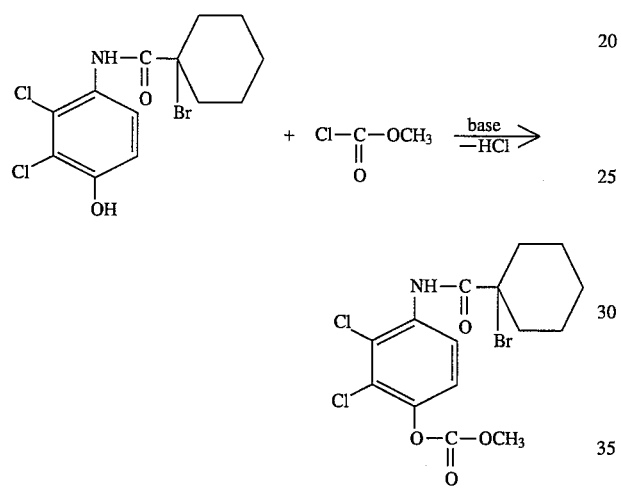

If 4-(1-bromo-cyclohexanoyl)-amino-2,3-dichloro-phenol is used as starting substance and thioethyl chloroformate as reactant, the course of the process according to the invention (second step, variant c) can be illustrated by the following equation:

If 4-(1-bromo-cyclohexanoyl)-amino-2,3-dichloro-phenol is used as starting substance and 2-methoxyethyl isocyanate as reactant, the course of the process according to the invention (second step, variant d) can be illustrated by the following equation:

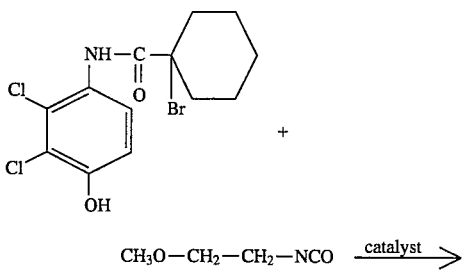

$$CH_3O-CH_2-CH_2-NCO \xrightarrow{catalyst}$$

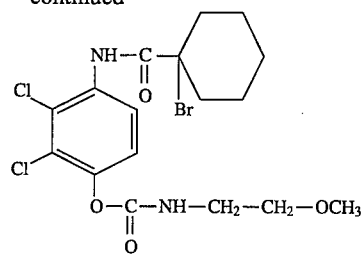

Formula (II) provides a general definition of the aminophenols required as starting substances for carrying out the process according to the invention (first step). In this formula, $X^1$, $X^2$, $X^3$ and $X^4$ preferably have those meanings which have already been mentioned in connection with the description of the substances of the formula (I) according to the invention as being preferred for these radicals.

The aminophenols of the formula (II) are known or can be prepared by methods known in principle (cf. EP-OS (European Published Specification) 0,416,365 and EP-OS (European Published Specification) 0,416,359).

Formula (III) provides a general definition of the cycloalkylcarboxylic acid derivatives furthermore required as starting substances for carrying out the process according to the invention (first step). In this formula, R, $R^1$, m and n preferably have those meanings which have already been mentioned in connection with the description of the substances of the formula (I) according to the invention as being preferred for these radicals and indices. Y preferably represents chlorine, bromine or a radical of the formula

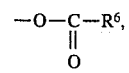

in which
$R^6$ is methyl, ethyl or

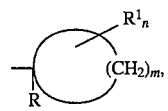

where R, $R^1$, m and n have the abovementioned meanings, or

Y represents the radicals of the formulae

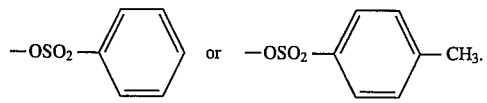

The cycloalkylcarboxylic acid derivatives of the formula (III) are known or can be prepared by methods known in principle (cf. J. Amer. Chem. Soc. 81, 2126 (1959)).

Acid-binding agents which are suitable for carrying out the process according to the invention (first step) are all customary inorganic and organic acid acceptors. The following can preferably be used: alkali metal carbonates and alkali metal alcoholates, such as sodium carbonate and potassium carbonate, sodium methylate, sodium ethylate, potassium methylate and potassium ethylate, distant aliphatic, aromatic and heterocyclic amines, for example triethylamine, trimethylamine, dimethylaniline, 1,8-diazabicyclo-(4,5,0)-undec-7-ene, dimethylbenzylamine and pyridine.

Diluents which are suitable for carrying out the process according to the invention (first step) are all customary inert organic solvents. The following can preferably be used: aliphatic and aromatic, optionally halogenated hydrocarbons, such as pentane, hexane, heptane, cyclohexane, petroleum ether, benzine, ligroin, toluene, xylene, methylene chloride, ethylene chlroid, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide dimethylacetamide and N-methylpyrrolidone, and also dimethyl sulphoxide, tetramethylene sulphone and hexamethylphosphoric triamide.

When carrying out the process according to the invention (first step), the reaction temperatures can be varied within a substantial range. In general, the process is carried out at temperatures between −20° C. and +120° C., preferably between 0° C. and +110° C.

The process according to the invention, both the first and the second steps (variant (a) to (d)) are generally carried out under atmospheric pressure. However, it is also possible to carry out each of these steps under increased or reduced pressure.

When carrying out the first step of the process according to the invention, 1 to 2 mol, preferably 1 to 1.4 mol, of cycloalkanecarboxylic acid derivative of the formula (III) is generally employed per mole of aminophenol of the formula (II). Working-up is carried out by customary methods.

The cycloalkanecarboxanilides of the formula (Ia), which are required as starting substances for carrying out the second step of the process according to the invention, are substances according to the invention.

Formula (IV) provides a general definition of the carboxylic acid halides required as reactants for carrying out the second step of the process according to the invention by variant (a). In this formula, $R^2$ preferably has those meanings, which have already been mentioned in connection with the description of the substances of the formula (I) according to the invention as being preferred for this radical. $Hal^1$ preferably represents chlorine or bromine.

The carboxylic acid halides of the formula (IV) are known or can be prepared by methods which are known in principle.

Suitable acid-binding agents for carrying out the second step of the process according to the invention by variant (a) are, again, all customary inorganic and organic acid acceptors. Substances which can preferably be used are those bases which have already been mentioned in connection with the procedure of the first step of the process according to the invention as being preferred.

Diluents which are suitable for carrying out the second step of the process according to the invention by variant (a) are, again, all customary inert organic solvents. Diluents which can preferably be used are those solvents which have already been mentioned in connection with the procedure of the first step of the process according to the invention as being preferred.

When carrying out the second step of the process according to the invention by variant (a), the reaction temperatures can also be varied within a substantial range. In general, the process is carried out at temperatures between −20° C. and +120° C., preferably between 0° C. and +110° C.

When carrying out the second step of the process according to the invention by variant (a), 1 to 2 mol, preferably 1 to 1.4 mol, of carboxylic acid halide of the formula (IV) are generally employed per mole of cycloalkanecarboxanilide of the formula (Ia). Working-up is carried out by customary methods.

Formula (V) provides a general definition of the halogenoformic esters required as reactants for carrying out the second step of the process according to the invention by variant (b). In this formula, $R^3$ preferably has those meanings which have already been mentioned in connection with the description of the substances of the formula (I) according to the invention as being preferred for this radical. $Hal^2$ preferably represents chlorine or bromine.

The halogenoformic esters of the formula (V) are known or can be prepared by methods which are known in principle.

Suitable acid-binding agents for carrying out the second step of the process according to the invention by variant (b) are, again, all customary inorganic and organic acid acceptors. Substances which can preferably be used are those bases which have already been mentioned in connection with the procedure of the first step of the process according to the invention as being preferred.

Diluents which are suitable for carrying out the second step of the process according to the invention by variant (b) are, again, all customary inert organic solvents. Diluents which can preferably be used are those solvents which have already been mentioned in connection with the procedure of the first step of the process according to the invention as being preferred.

When carrying out the second step of the process according to the invention by variant (b), the reaction temperatures can also be varied within a substantial range. In general, the process is carried out at temperatures between −20° C. and +120° C., preferably between 0° C. and +110° C.

When carrying out the second step of the process according to the invention by variant (b), 1 to 2 mol, preferably 1 to 1.4 mol, of halogenoformic ester of the formula (V) are generally employed per mole of cycloalkanecarboxanilide of the formula (Ia). Working-up is carried out by customary methods.

Formula (VI) provides a general definition of the haloformic esters required as reactants for carrying out the second step of the process according to the invention by variant (c). In this formula, $R^4$ preferably has those meanings which have already been mentioned in connection with the description of the substances of the formula (I) according to the invention as being preferred for this radical. $Hal^1$ preferably represents chlorine or bromine.

The halogenoformic thioesters of the formula (VI) are known or can be prepared by methods which are known in principle.

Suitable acid-binding agents for carrying out the second step of the process according to the invention by variant (c) are, again, all customary inorganic and organic acid acceptors. Substances which can preferably be used are those bases which have already been mentioned in connection with the procedure of the first step of the process according to the invention as being preferred.

Diluents which are suitable for carrying out the second step of the process according to the invention by variant (c) are, again, all customary inert organic solvents. Diluents which can preferably be used are those solvents which have already been mentioned in connection with the procedure of the first step of the process according to the invention as being preferred.

When carrying out the second step of the process according to the invention by variant (c), the reaction temperatures can also be varied within a substantial range. In general, the process is carried out at temperatures between −20° C. and +120° C., preferably between 0° C. and +110° C.

When carrying out the second step of the process according to the invention by variant (c), 1 to 2 mol, preferably 1 to 1.4 mol, of halogenoformic thioester of the formula (VI) are generally employed per mole of cycloalkanecarboxanilide of the formula (Ia). Working-up is carried out by customary methods.

Formula (VII) provides a general definition of the isocyanates required as reactants for carrying out the second step of the process according to the invention by variant (d). In this formula, $R^5$ preferably has those meanings which have already been mentioned in connection with the description of the substances of the formula (I) according to the invention as being preferred for this radical.

The isocyanates of the formula (VII) are known or can be prepared by methods which are known in principle.

Suitable catalysts for carrying out the second step of the process according to the invention by variant (d) are all reaction accelerators which are customary for such reactions. Cyclic amines, such as, for example, 1,8-diazabicyclo[5,4,0]-undec-7-ene, can preferably be used.

Suitable diluents for carrying out the second step of the process according to the invention by variant (d) are all inert organic solvents which are customary for such reactions. The following can preferably be used: aliphatic and aromatic hydrocarbons, such as pentane, hexane, heptane, cyclohexane, petroleum ether, benzine, ligroin, toluene, xylene, or ethers, such as diethyl ether, dibutyl ether, glycol dimethyl ether, diglycol dimethyl ether, tetrahydrofuran and dioxane.

When carrying out the second step of the process according to the invention by variant (d), the reaction temperatures can also be varied within a substantial range. In general, the process is carried out at temperatures between −20° C. and +120° C., preferably between 0° C. and +110° C.

When carrying out the second step of the process according to the invention by variant (d), 1 to 2 mol, preferably 1 to 1.4 mol, of isocyanate of the formula (VII) and a small amount of catalyst are generally employed per mole of cycloalkanecarboxanilide of the formula (Ia). Working-up is carried out by customary methods.

The substances according to the invention are suitable as pesticides, in particular as fungicides.

Fungicides in plant protection are employed for combating Plasmadiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:
Xanthomonas species, such as Xanthomonas oryzae;
Pseudomonas species, such as Pseudomonas lachrymans;
Erwinia species, such as Erwinia amylovora;
Pythium species, such as Pythium ultimum;
Phytophthora species, such as Phytophthora infestans;
Pseudoperonospora species, such as Pseudoperonospora humuli or Pseudoperonospora cubensis;
plasmopara species, such as Plasmopara viticola;
Peronospora species, such as Peronospora pisi or P. brassicae;
Erysiphe species, such as Erysiphe graminis;
Sphaerotheca species, such as Sphaerotheca fuliginea;
Podosphaera species, such as Podosphaera leucotricha;
Venturia species, such as Venturia inaequalis;
Pyrenophora species, such as Pyrenophora teres or P. graminea; (conidia form: Drechslera, syn: Helminthosporium);
Cochliobolus species, such as Cochliobolus sativus; (conidia form: Drechslera, syn: Helminthosporium);
Uromyces species, such as Uromyces appendiculatus;
Puccinia species, such as Puccinia recondita;
Tilletia species, such as Tilletia caries;
Ustilago species, such as Ustilago nuda or Ustilago avenae;
Pellicularia species, such as Pellicularia sasakii;
Pyricularia species, such as Pyricularia oryzae;
Fusarium species, such as Fusarium culmorum;
Botrytis species, such as Botrytis cinerea;
Septoria species, such as Septoria nodorum;
Leptosphaeria species, such as Leptsophaeria nodorum;
Cercospora species, such as Cercospora canescens;
Alternaria species, such as Alternaria brassicae and Pseudocercosporella species, such as Pseudocercosporella herpotrichoides.

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating Botrytis. Moreover, they have a good in-vitro activity.

The substances according to the invention can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks, such as calcite, marble, pumice, sepiolite and dolomite, as well as synthetic granules of inorganic and organic meals, and granules of organic material, such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives, such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants, such as inorganic pigments, for example iron oxide, titanium oxide and Prussian Blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

When using the substances according to the invention, the application rate can be varied within a substantial range depending on the way of application. For example, in the treatment of parts of plants, the active compound concentrations in the use forms are, in general, between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02% by weight, are required at the place of action.

The preparation and the use of the substances according to the invention can be seen from the Examples which follow.

PREPARATION EXAMPLES

Example 1

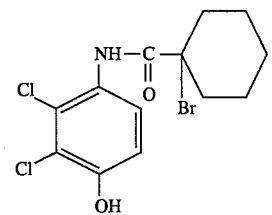

12.6 g (0.056 mol) of 1-bromo-cyclohexanecarboxylic acid chloride are added dropwise at 0° C. with stirring to a mixture of 10 g (0.056 mol) of 4-amino-2,3-dichlorophenol and 100 ml of tetrahydrofuran. After adding half (5 g) of the acid chloride, 7.7 ml (0.05 mol) of triethylamine are added dropwise at the same time. When the addition has ended, the reaction mixture is stirred for 24 hours at 20° C. and then poured into 300 ml of ice-water. The mixture is extracted twice using in each case 300 ml of dichloromethane, and the organic phase is dried over magnesium sulphate and evaporated by stripping off the solvent under reduced pressure. The residue which remains is recrystallized from toluene. In this manner, 11.9 g (58% of theory) of 4-(1-bromo-cyclohexanoyl)-amino-2,3-dichloro-phenol are obtained in the form of a solid substance of melting point 142° C.

Example 2

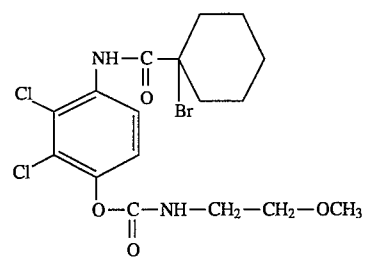

0.6 g (6 mmol) of 2-methoxyethyl isocyanate is added with stirring at room temperature to a solution of 2 g (5.5 mmol) of 4-(1-bromocyclohexanoyl)-amino-2,3-dichloro-phenol in 10 ml of toluene. 30 mg (0.2 mmol) of 1,8-diaza-bicyclo[5,4,0]undec-7-ene (DBU) are then added at room temperature with stirring. Stirring is continued for 24 hours at 50° C., and the solvent is then distilled off under reduced pressure. The residue which remains is chromatographed on silica gel using toluene:ethyl acetate=7:3. In this manner, 1.6 g (64% of theory) of 4-(2-methoxy-ethyl-amino-carbonyloxy)-2,3-dichloro(1-bromo-cyclohexanoic acid) anilide are obtained in the form of a solid substance of melting point 75° C.

Example 3

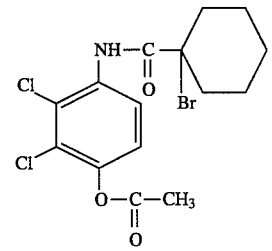

0.5 g (6 mmol) of acetyl chloride is slowly added dropwise at 20° C. with stirring to a mixture of 2 g (5.5 mmol) of 4-(1-bromo-cyclohexanoyl)-amino-2,3-dichloro-phenol, 0.8 ml (6 mmol) of triethylamine and 10 ml of tetrahydrofuran. After the addition has ended, the reaction mixture is stirred for 24 hours at 20° C. and then poured into 100 ml of ice-water. The solid obtained is filtered off, dried and recrystallized from toluene/hexane. In this manner, 2 g (90% of theory) of 4-acetyl-oxy-2,3-dichloro-(1-bromo-cyclohexanoic acid) anilide are obtained in the form of a solid substance of melting point 129° C.

The substances listed in the table below are also prepared by the above-described methods.

TABLE 1

$$\text{(I)}$$

Structure: Aryl ring with substituents $X^1$, $X^2$, $X^3$, $X^4$ and OZ, bearing NH-C(=O)-CR(R$^1_n$)(CH$_2$)$_m$ group.

| Example No. | $X^1$ | $X^2$ | $X^3$ | $X^4$ | R group (cyclic with $R^1_n$, (CH$_2$)$_m$) | Z | Melting Point [°C.] |
|---|---|---|---|---|---|---|---|
| 4 | Cl | Cl | H | H | 1-Br-cyclohexyl | $-\underset{\overset{\|}{O}}{C}-OCH_2-CH_2-OCH_3$ | 86 |
| 5 | Cl | Cl | H | H | " | $-\underset{\overset{\|}{O}}{C}-SC_2H_5$ | 90 |
| 6 | Cl | Cl | H | H | " | $-\underset{\overset{\|}{O}}{C}-OCH_3$ | 110 |
| 7 | Cl | Cl | H | H | 1-Cl-cyclohexyl | $-\underset{\overset{\|}{O}}{C}-OCH_2-CH_2-OCH_3$ | |
| 8 | Cl | Cl | H | H | " | $-\underset{\overset{\|}{O}}{C}-SC_2H_5$ | |
| 9 | Cl | Cl | H | H | " | $-\underset{\overset{\|}{O}}{C}-OCH_3$ | |
| 10 | Cl | Cl | H | H | 1-Br-cyclopentyl | $-\underset{\overset{\|}{O}}{C}-OCH_2-CH_2-OCH_3$ | |
| 11 | Cl | Cl | H | H | " | $-\underset{\overset{\|}{O}}{C}-SC_2H_5$ | |
| 12 | Cl | Cl | H | H | 1-Br-cyclopentyl | $-\underset{\overset{\|}{O}}{C}-OCH_3$ | |
| 13 | Cl | Cl | H | H | 1-Cl-cyclohexyl | H | |
| 14 | Cl | Cl | H | H | 1-Br-cyclopentyl | H | |
| 15 | Cl | Cl | H | H | 1-Cl-cyclopentyl | H | |

Example A

Botrytis test (dwarf bean)/protective

Solvent: 4.7 parts by weight of acetone

Emulsifier: 0.3 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small agar pieces covered in growth of Botrytis cinerea are placed onto each leaf. The inoculated plants are placed in a darkened, humid chamber at 20° C. 3 days after the inoculation, the size of the lesions on the leaves are evaluated.

In this test, a degree of effectiveness of over 90% is shown by the substances (1) to (6) according to the invention at a concentration of 100 ppm in the spray liquor.

We claim:

1. Cycloalkylcarboxanilides of the formula

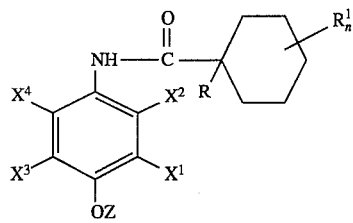

in which

R represents halogen or halogenoalkyl, $R^1$ represents halogen, alkyl or halogenoalkyl, n represents the numbers 0, 1, 2 or 3, $X^1$, $X^2$, $X^3$ and $X^4$ independently of one another represent hydrogen, halogen, alkyl, halogenoalkyl, alkoxy, halogenoalkoxy, alkylthio or halogenoalkylthio, and Z represents hydrogen.

2. Cycloalkylcarboxanilides of the formula (I) according to claim 1, in which

R represents fluorine, chlorine, bromine, iodine or halogenoalkyl having 1 to 3 carbon atoms and 1 to 5 identical or different halogen atoms, $R^1$ represents fluorine, chlorine, bromine, straight-chain or branched alkyl having 1 to 4 carbon atoms or halogenoalkyl having 1 to 3 carbon atoms and 1 to 5 identical or different halogen atoms, n represents the numbers 0, 1, 2 and 3, $X^1$ represents hydrogen, fluorine, chlorine, bromine, iodine, straight-chain or branched alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms or halogenoalkylthio having 1 to 3 carbon atoms and 1 to 5 identical or different halogen atoms, $X^2$ represents hydrogen, fluorine, chlorine, bromine, iodine, straight-chain or branched alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms or halogenoalkylthio having 1 to 3 carbon atoms and 1 to 5 identical or different halogen atoms, $X^3$ represents hydrogen, fluorine, chlorine, bromine, iodine, straight-chain or branched alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms or halogenoalkylthio having 1 to 3 carbon atoms and 1 to 5 identical or different halogen atoms.

$X^4$ represents hydrogen, straight-chain or branched alkyl having 1 to 4 carbon atoms, halogenoalkyl having 1 to 3 carbon atoms and 1 to 5 identical or different halogen atoms, alkoxy having 1 to 4 carbon atoms, halogenoalkoxy having 1 to 3 carbon atoms and 1 to 5 identical or different halogen atoms, alkylthio having 1 to 4 carbon atoms or halogenoalkylthio having 1 to 3 carbon atoms and 1 to 5 identical or different halogen atoms.

3. Cycloalkylcarboxanilides of the formula (I) according to claim 1, in which

R represents fluorine, chlorine, bromine, iodine, trifluoromethyl, trichloromethyl, difluoromethyl, fluoromethyl or fluorochloromethyl.

$R^1$ represents fluorine, chlorine, bromine, methyl, ethyl, n-propyl, isopropyl, n-butyl, tert.-butyl, trifluoromethyl, trichloromethyl, difluoromethyl, fluoromethyl or fluorochloromethyl, n represents the numbers 0, 1, 2 or 3, $X^1$ represents hydrogen, fluorine, chlorine, bromine, iodine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio or trifluoromethylthio, $X^2$ represents hydrogen, fluorine, chlorine, bromine, iodine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio or trifluoromethylthio, $X^3$ represents hydrogen, fluorine, chlorine, bromine, iodine, methyl, ethyl, n-propyl, isopropyl, n-butyl, tert.-buty, trifluoromethyl, trichloromethyl, difluoromethyl, fluoromethyl, fluorochloromethyl, methoxy, ethoxy, trifluoromethoxy, methylthio, ethylthio or trifluoromethylthio, $X^4$ represents hydrogen, fluorine, chlorine, bromine, iodine, methyl, ethyl, n-propyl, isopropyl, n-butyl, tert.-butyl, trifluoromethyl, trichloromethyl, difluoromethyl, fluoromethyl, fluorochloromethyl, methoxy, ethoxy, trifluoromethoxy, methylthio, ethylthio or trifluoromethylthio.

4. A cycloalkylcarboxanilide of the formula (I) according to claim 1, in which n represents 0, $X_1$ represents chlorine, $X_2$ represents chlorine, R represents chlorine, bromine or trifluoromethyl.

5. A cycloalkylcarboxanilide according to claim 1, of the formula

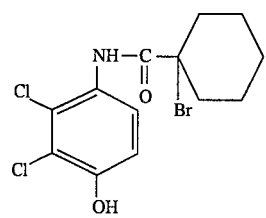
6. A pesticidal composition comprising a pesticidally effective amount of a cycloalkylcarboxanilide according to claim 1 and a diluent.
7. Method of combating pests, characterized in that cycloalkylcarboxanilides of the formula (I) according to claim 1 are applied to the pests and/or their environment.
* * * * *